(12) United States Patent
Yaguchi

(10) Patent No.: US 10,842,364 B2
(45) Date of Patent: Nov. 24, 2020

(54) IMAGE PROCESSING DEVICE, ENDOSCOPE APPARATUS, INFORMATION STORAGE DEVICE, AND IMAGE PROCESSING METHOD

(71) Applicant: OLYMPUS CORPORATION, Hachioji (JP)

(72) Inventor: Yoichi Yaguchi, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 195 days.

(21) Appl. No.: 15/836,750

(22) Filed: Dec. 8, 2017

(65) Prior Publication Data

US 2018/0092518 A1 Apr. 5, 2018

Related U.S. Application Data

(63) Continuation of application No. PCT/JP2015/068186, filed on Jun. 24, 2015.

(51) Int. Cl.
*A61B 1/04* (2006.01)
*A61B 1/00* (2006.01)
(Continued)

(52) U.S. Cl.
CPC ........ *A61B 1/041* (2013.01); *A61B 1/00009* (2013.01); *A61B 1/042* (2013.01); *G06K 9/00* (2013.01); *G06K 9/4604* (2013.01); *G06K 9/6224* (2013.01); *G06T 7/0012* (2013.01); *G06T 7/11* (2017.01); *G06T 7/12* (2017.01);
(Continued)

(58) Field of Classification Search
CPC ..... A61B 1/041; A61B 1/00009; A61B 1/042; G06K 9/6224; G06K 9/4604; G06K 9/00; G06K 2209/051; G06T 2207/30004; G06T 7/64; G06T 7/60; G06T 7/0012;
(Continued)

(56) References Cited

U.S. PATENT DOCUMENTS 10,121,243 B2 * 11/2018 Boroczky .............. G16H 50/30
10,395,363 B2 * 8/2019 Sakimoto .................. G06T 7/12
(Continued)

FOREIGN PATENT DOCUMENTS

JP 2010187756 A 9/2010
JP 2012120799 A 6/2012
JP 2012125469 A 7/2012

OTHER PUBLICATIONS

International Search Report (ISR) and Written Opinion dated Sep. 29, 2015 issued in International Application No. PCT/JP2015/068186.

(Continued)

*Primary Examiner* — Joseph W Becker
(74) *Attorney, Agent, or Firm* — Holtz, Holtz & Volek PC

(57) ABSTRACT

An image processing device includes a processor including hardware, the processor being configured to: acquire an input image; detect an arc curve in the input image; determine a change in a luminance of a pixel in a direction from an inner side toward an outer side of the arc curve; detect, as a representative bubble region, a region including the arc curve involving a change determined to be an increase in the luminance in the direction from the inner side toward the outer side; and extract a bubble region, based on the representative bubble region.

4 Claims, 12 Drawing Sheets

(51) Int. Cl.
| | |
|---|---|
| *G06K 9/00* | (2006.01) |
| *G06T 7/64* | (2017.01) |
| *G06K 9/46* | (2006.01) |
| *G06K 9/62* | (2006.01) |
| *G06T 7/136* | (2017.01) |
| *G06T 7/12* | (2017.01) |
| *G06T 7/11* | (2017.01) |
| *G06T 7/00* | (2017.01) |
| *G06T 7/60* | (2017.01) |

(52) U.S. Cl.
 CPC ............... *G06T 7/136* (2017.01); *G06T 7/60* (2013.01); *G06T 7/64* (2017.01); *G06K 2209/051* (2013.01); *G06T 2207/10024* (2013.01); *G06T 2207/10068* (2013.01); *G06T 2207/30004* (2013.01)

(58) Field of Classification Search
 CPC ... G06T 7/11; G06T 7/12; G06T 7/136; G06T 2207/10068; G06T 2207/10024
 See application file for complete search history.

(56) References Cited

U.S. PATENT DOCUMENTS

| | | |
|---|---|---|
| 2010/0208047 A1 | 8/2010 | Kitamura |
| 2012/0148153 A1* | 6/2012 | Kitamura ................ G06T 7/60 |
| | | 382/165 |
| 2012/0155724 A1 | 6/2012 | Kitamura et al. |

OTHER PUBLICATIONS

Viorica Patraucean, et al., "A Parameterless Line Segment and Elliptical Arc Detector with Enhanced Ellipse Fitting," Computer Vision—ECCV 2012 Lecture Notes in Computer Science 2012, pp. 572-585.

* cited by examiner

IMAGE PROCESSING DEVICE, ENDOSCOPE APPARATUS, INFORMATION STORAGE DEVICE, AND IMAGE PROCESSING METHOD

CROSS REFERENCE TO RELATED APPLICATION

This application is a continuation of International Patent Application No. PCT/JP2015/068186, having an international filing date of Jun. 24, 2015, which designated the United States, the entirety of which is incorporated herein by reference.

BACKGROUND

Conventionally, there has been a demand for detecting a bubble in an image that has been input, that is, a demand for extracting a bubble region as a region corresponding to a captured image of the bubble in the input image. In particular, there has been a demand for extracting a bubble region, from an in-vivo image obtained by capturing an image inside the body of an examinee (patient), to be distinguished from a mucous membrane region.

For example, JP-A-2012-125469 discloses a method including: detecting a candidate point forming a bubble shape in an image; and detecting a circular shape, to be extracted as a bubble region, based on the candidate point.

Viorica Patraucean, Pierre Gurdjos, Rafael Grompone von Gioi "A Parameterless Line Segment and Elliptical Arc Detector with Enhanced Ellipse Fitting" Computer Vision—ECCV 2012 Lecture Notes in Computer Science 2012, pp. 572-585 discloses a method with which an arc curve can be detected without requiring complex parameter setting.

SUMMARY

According to one aspect of the invention, there is provided an image processing device comprising a processor including hardware, the processor being configured to:
acquire an input image;
detect an arc curve in the input image;
determine a change in a luminance of a pixel in a direction from an inner side toward an outer side of the arc curve;
detect, as a representative bubble region, a region including the arc curve involving a change determined to be an increase in the luminance in the direction from the inner side toward the outer side; and
extract a bubble region from the input image, based on the representative bubble region.

According to another aspect of the invention, there is provided an endoscope apparatus comprising the above image processing device.

According to another aspect of the invention, there is provided an information storage device storing a program,
the program causing a computer to execute:
acquiring an input image;
detecting an arc curve in the input image;
determining whether or not a luminance of a pixel in an inner side of the arc curve is darker than a luminance of a pixel in an outer side of the arc curve;
detecting, as a representative bubble region, a region including the arc curve involving a change determined to be an increase in the luminance in the direction from the inner side toward the outer side; and
extracting a bubble region from the input image, based on the representative bubble region.

According to another aspect of the invention, there is provided an image processing method comprising: detecting an arc curve in the input image;
determining whether or not a luminance of a pixel in an inner side of the arc curve is darker than a luminance of a pixel in an outer side of the arc curve;
detecting, as a representative bubble region, a region including the arc curve involving a change determined to be an increase in the luminance in the direction from the inner side toward the outer side; and
extracting a bubble region from the input image, based on the representative bubble region.

DESCRIPTION OF EXEMPLARY EMBODIMENTS

Figure 1A:
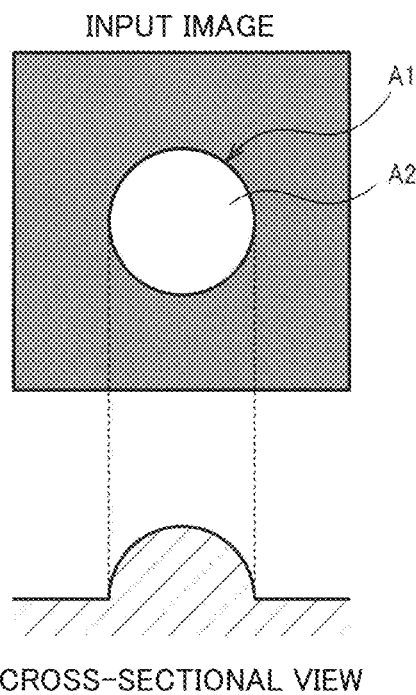
FIG. 1A illustrates an example of an arc curve corresponding to a non-bubble structure.

JP-A-2012-125469 involves a risk of erroneously extracting a non-bubble structure having a circular shape as a bubble region. Viorica Patraucean et al.,1 involves detection of an arc curve, but whether or not the arc curve is a part of a bubble or a non-bubble structure is not taken into consideration. In fact, no conventional method of performing a process based on brightness (luminance) of an image on the inner and the outer sides of the arc curve as a part of a bubble has been disclosed.

According to one embodiment of the invention, there is provided an image processing device comprising a processor including hardware, the processor being configured to:

acquire an input image;

detect an arc curve in the input image;

determine a change in a luminance of a pixel in a direction from an inner side toward an outer side of the arc curve;

detect, as a representative bubble region, a region including the arc curve involving a change determined to be an increase in the luminance in the direction from the inner side toward the outer side; and extract a bubble region from the input image, based on the representative bubble region.

In the present embodiment, a representative bubble region is detected based on a change in a luminance between the inner and the outer sides of an arc curve, and the bubble region is extracted based on the representative bubble region. With this configuration, the representative bubble region can be detected based on the luminance change unique to the bubble region, whereby more accurate bubble region extraction and the like can be achieved.

In the image processing device, the processor may determine a similarity between a gradient direction of a pixel value on the arc curve and a direction away from a center of the arc curve; and determine that the change is the increase in the luminance in the direction from the inner side toward the outer side, when the similarity is determined to be high.

With this configuration, the luminance change between the inner and the outer sides of the arc curve can be determined based on the similarity between the gradient direction and the direction away from the center.

In the image processing device, the processor may detect the arc curve by combining a plurality of pixels the gradient directions of which have been determined to be similar to each other.

With this configuration, in the arc curve detection stage, an arc curve having pixels with similar gradient directions can be set as the detection target.

In the image processing device, the processor may determine whether or not the change is the increase in the luminance in the direction from the inner side toward the outer side of the arc curve, by determining the similarity between the gradient direction at a target pixel in the arc curve and the direction away from the center at the target pixel.

With this configuration, the luminance change between the inner and the outer sides of the arc curve can be determined based on the similarity between the gradient direction and the direction away from the center at the target pixel.

In the image processing device, the processor may extract a region including the representative bubble region as the bubble region.

With this configuration, the region including the representative bubble region can be extracted as the bubble region.

In the image processing device, the processor may obtain a bubble region feature value based on a feature value of a pixel in the representative bubble region; and extract, as the bubble region, a group of pixels, in pixels in the input image, each having the feature value determined to be similar to the bubble region feature value.

With this configuration, the bubble region can be extracted based on the similarity between the bubble region feature value obtained from the representative bubble region and the feature value of each pixel.

In the image processing device, the processor may extract, by segmenting the input image into regions by a graph cut process based on the bubble region feature value, a region including the representative bubble region as the bubble region.

With this configuration, the bubble region can be extracted through the graph cut process.

In the image processing device, the processor may set a value based on a similarity between the feature value of a pixel in the input image and the bubble region feature value, as a cost for a link establishing connection between a node representing the representative bubble region and a node representing the pixel in the input image; and execute the graph cut process based on the cost.

With this configuration, the cost (energy) used for the graph cut process can be set based on the similarity between the bubble region feature value and the feature value of each pixel.

In the image processing device, the processor may extract, as the bubble region, a group of pixels, in pixels in the input image, each having the feature value with a similarity to the bubble region feature value equal to or higher than a given threshold value.

With this configuration, the bubble region can be extracted based on threshold value determination using the similarity between the bubble region feature value and the feature value of each pixel.

In the image processing device, the processor may calculate the feature value based on a pixel value and coordinates, the bubble region feature value may be a function approximating a distribution of the feature quantities of pixels in the representative bubble region.

With this configuration, the pixel value and the coordinates of the pixel may be used as the feature value, and the function approximating the distribution of the feature quantities can be used as the bubble region feature value.

In the image processing device, the processor may detect, as the representative bubble region, a region including the arc curve having a central angle that is equal to or larger than a given threshold value.

With this configuration, the representative bubble region can be detected based on the central angle of the arc curve.

In the image processing device, the processor may detect, as the representative bubble region, a region including the arc curve with a radius within a given range.

With this configuration, the representative bubble region can be detected based on the radius of the arc curve.

In the image processing device, the input image may be an in-vivo image, the processor may perform a process of detecting a region of interest from a region in the in-vivo image excluding the bubble region extracted.

With this configuration, a result of extracting the bubble region can be used for the process of detecting the region of interest.

According to another embodiment of the invention, there is provided an image processing device comprising a processor including hardware, the processor being configured to:

acquire an input image;

detect arc curves in the input image;

detect, as a representative bubble region, a region including at least a part of the arc curves;

obtain a bubble region feature value based on a feature value of a pixel in the representative bubble region; and extract, by segmenting the input image into regions by a graph cut process based on the bubble region feature value, the bubble region from the input image.

In the other embodiment of the present invention, the representative bubble region is detected from the arc curve, and the bubble region is extracted through the graph cut process using the bubble region feature value obtained based on the representative bubble region. With this configuration, the bubble region can be extracted based on the graph cut process.

According to another embodiment of the invention, there is provided an endoscope apparatus comprising the above image processing device.

According to another embodiment of the invention, there is provided an information storage device storing a program, the program causing a computer to execute:

acquiring an input image;

detecting an arc curve in the input image;

determining whether or not a luminance of a pixel in an inner side of the arc curve is darker than a luminance of a pixel in an outer side of the arc curve;

detecting, as a representative bubble region, a region including the arc curve involving a change determined to be an increase in the luminance in the direction from the inner side toward the outer side; and extracting a bubble region from the input image, based on the representative bubble region.

According to another embodiment of the invention, there is provided an image processing method comprising: detecting an arc curve in the input image;

determining whether or not a luminance of a pixel in an inner side of the arc curve is darker than a luminance of a pixel in an outer side of the arc curve;

detecting, as a representative bubble region, a region including the arc curve involving a change determined to be an increase in the luminance in the direction from the inner side toward the outer side; and extracting a bubble region from the input image, based on the representative bubble region.

The exemplary embodiments of the invention are described below. Note that the following exemplary embodiments do not in any way limit the scope of the invention laid out in the claims. Note also that not all of the elements described below in connection with the exemplary embodiments should be taken as essential elements of the invention.

1. Method According to Present Embodiment

First of all, a method according to the present invention is described. As described above, there has been a demand for extracting a bubble region from an input image. For example, the bubble region may be extracted to be treated as a non-required region. For example, bubbles might hinder the observation of an object behind the bubbles (an object that is in the same direction as the bubbles as viewed from an imaging section and is farther from the imaging section than the bubbles) in an input image. Thus, the bubble region is extracted, so that the region to be observed on the input image can be limited to a region other than the bubble region, whereby a load on an observer (a person viewing the image) can be reduced. Alternatively, the bubble region may be extracted from a region that is a target of image processing for object detection or the like, whereby the processing load can be reduced.

In this context, JP-A-2012-125469 discloses a method of extracting the bubble region by detecting a circular region. Unfortunately, the method of extracting the bubble region in JP-A-2012-125469, which is based on a process of detecting a circular shape, might result in detection of a non-bubble structure that has a circular shape on the image. For example, FIG. 1A is a cross-sectional front view illustrating an image of a generally planer object partially including a convex-shape portion protruding beyond the other portion. In this case, a boundary between the planer portion and the convex-shape portion is likely to be detected as an edge on the image. Thus, an arc curve A1 is detected on the input image as illustrated in FIG. 1A, whereby the conventional method has a risk of detecting a non-bubble structure as a bubble.

JP-A-2012-125469 also discloses a method of detecting a specular-reflection region with a high luminance, and determining that a circular shape corresponding to a bubble is in the neighborhood of the region. For example, light is likely to be incident on the structure protruding toward the imaging section as illustrated in FIG. 1A, and reflected light from the convex portion is likely to reach the imaging section, and thus the convex structure is likely to be bright in the captured image. Thus, the non-bubble structure may have a high-luminance (bright) region, as represented by an inside portion A2 of the arc curve, in the neighborhood of the arc curve. All things considered, the determination based on a high-luminance portion is not free of the risk of erroneously detecting a non-bubble structure as a bubble.

In view of the above, the present applicant proposes a method of extracting a bubble region with a risk of erroneously detecting a structure illustrated in FIG. 1A or the like as a bubble reduced. The present applicant has focused on a luminance characteristic that is almost an exclusive feature of bubble structures. Specifically, an arc curve formed due to a bubble structure is characterized in that the inner side of the arc curve is dark (low luminance) and the outer side of the arc curve is bright (high luminance). The arc curve might not necessarily have a closed structure (may be a part of a true circle or an ellipse). In such a case, the inner side and the outer side of a circular shape defined by the arc curve may be respectively considered as the inner side and the outer side of the arc curve.

Figure 1B:
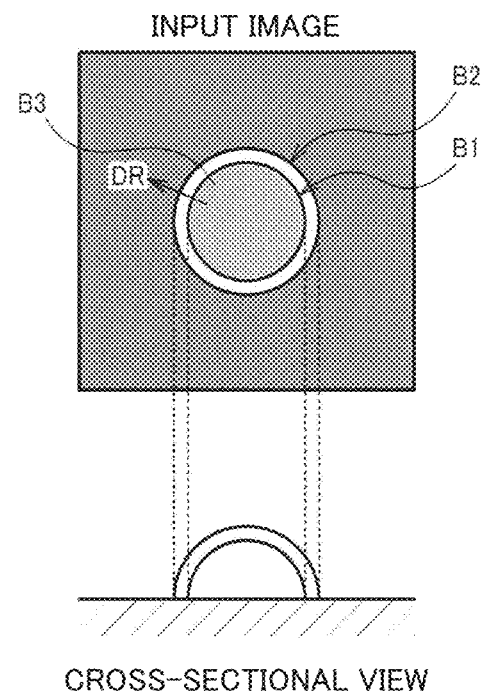
FIG. 1B illustrates an example of an arc curve corresponding to a bubble.

FIG. 1B illustrates a specific example. A boundary portion of a bubble appears to be bright in the captured image due to an influence of reflected light from the film. Assuming that the film portion has a certain thickness, the input image includes an arc curve B1 corresponding to the inner side of the film and an arc curve B2 corresponding to the outer side of the film. Further assuming that no specular reflection occurs on a portion on the inner side of the arc curve B1, the region (B3) involves a lower chance of the reflected light from the film reaching the imaging section and refraction of light at the film, and thus appears to be darker in the image than the arch portion.

Figure 2:
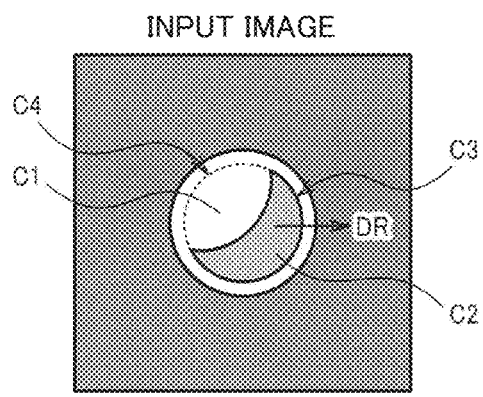
FIG. 2 illustrates an example of an arc curve in a case where specular reflection occurs on a bubble.

As illustrated in FIG. 2, a portion where the specular reflection occurs has an extremely high luminance (C1). Still, the specular reflection is less likely to occur over the entire portion on the inner side of the arc curve, because the bubble has a spherical shape due to the surface tension.

Thus, the region on the inner side of the arc curve is expected to at least partially include a dark region (C2 in FIG. 2) as in B3 in FIG. 1B.

Specifically, the luminance of a pixel changes to increase along a direction DR from the inner side toward the outer side of the arc curve B1 in the input image illustrated in FIG. 1B or the arc curve C3 in the input image illustrated in FIG. 2. On the other hand, in a typical non-bubble structure that appears to have a circular shape as illustrated in FIG. 1A, the opposite luminance change occurs. More specifically, the luminance of a pixel changes to decrease along a direction from the inner side toward the outer side of the arc curve. Thus, a bubble that is a detection target and a non-bubble structure that is not a detection target are different from each other in how the luminance tends to be different between the inner and the outer sides of the arc curve. Based on this, accurate bubble detection can be achieved.

The present applicant has made research to find out that there is almost no structure, other than the bubble structure, with an arc curve involving a change in the luminance increasing in a direction from the inner side toward the outer side. All things considered, determination based on the change in the luminance as described above can reduce a risk of erroneously detecting structures (non-bubble structures including an arc curve) other than that in FIG. 1A as a bubble.

Figure 3:
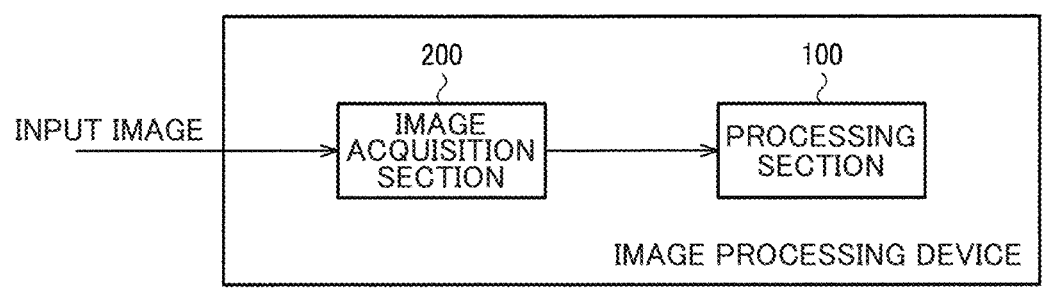
FIG. 3 illustrates a configuration example of an image processing device according to the present embodiment.

Specifically, as illustrated in FIG. 3, an image processing device according to the present embodiment includes: an image acquisition section 200 that acquires an input image; and a processing section 100 that performs a process of extracting a bubble region from the input image. The processing section 100 performs: detection of an arc curve from the input image; determination on a change in a pixel luminance in a direction from the inner side toward the outer side of the arc curve; detection of a region including an arc curve determined to involve a change in the luminance increasing from the inner side toward the outer side as a representative bubble region; and extraction of a bubble region from the input image based on the representative bubble region.

As used in the present embodiment, the term "arc curve" is a curve representing at least a part of a circle or an ellipse. Thus, the arc curve according to the present embodiment may be a true circle or an ellipse (central angle=360°), or may be a curve corresponding to a part of a contour of the true circle or the ellipse (central angle<360°). The arc curve is not limited to a curve completely conforming to a part of the true circle or the ellipse, and may partially have a recess, a protrusion, or a distortion. The arc curve may also be limited to the true circle, a part of the true circle, or other like shapes. The calculation load can be reduced with the ellipse, a part of the ellipse, or other like shapes excluded from the processing target.

Figure 6A:
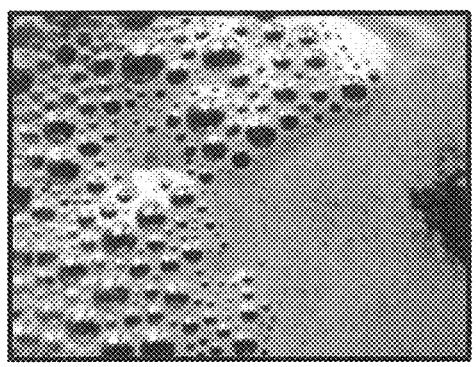
FIG. 6A illustrates an example of an input image.
Figure 6B:
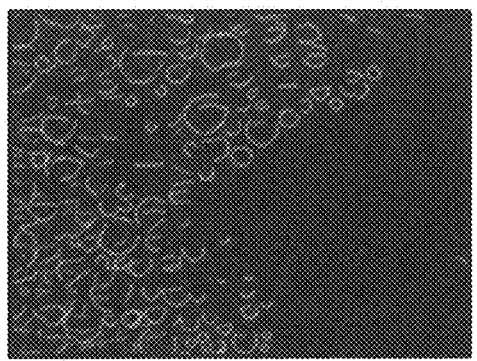
FIG. 6B illustrates an example of a result of an arc curve detection process.
Figure 6C:
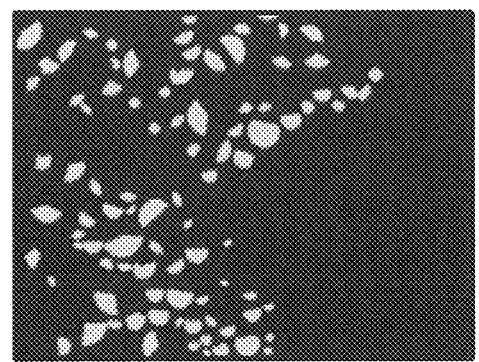
FIG. 6C illustrates an example of a result of a representative bubble region detection process.
Figure 6D:
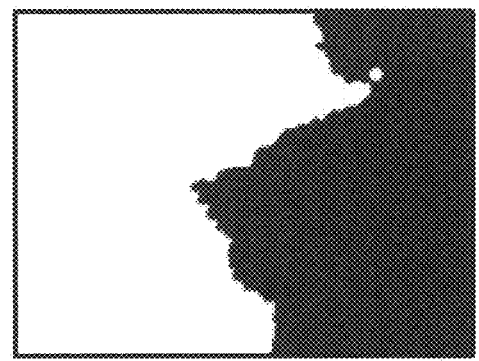
FIG. 6D illustrates an example of a result of a bubble region extraction process.

A method according to the present embodiment includes extracting the representative bubble region. For example, a captured image illustrated in FIG. 6A, described later, has a representative bubble region as illustrated in FIG. 6C. As indicated by C1 in FIG. 2, even a region on the inner side of the arc curve, representing a bubble, may have an extremely high luminance due to an occurrence of the specular reflection. Thus, as indicated by C4 in FIG. 2, the arc curve might be undetectable due to the absence of a difference in luminance from the boundary portion of the bubble in the first place. Even when the arc curve is successfully detected on the boundary portion, the arc curve involves a change in the luminance decreasing from the inner side toward the outer side of the arc curve. Thus, the region C1 is a bubble region, but is not detected as the representative bubble region, and this is tolerated in the present embodiment. In other words, the representative bubble region according to the present embodiment is a representative region of the bubble region, more specifically, a region in the input image that is likely to be the bubble region. Thus, the bubble region does not necessarily need to be entirely detected as the representative bubble region. The image illustrated in FIG. 6A includes a bubble region to be finally extracted as illustrated in FIG. 6D. Thus, a process of obtaining the region in FIG. 6D from an image in FIG. 6C is executed (in a narrow sense, a bubble region extraction process). The bubble region extraction process is described in detail later.

The bubble, in the image, has a shape with double arc curves (B1 and B2) due to the thickness of the film of the bubble. In the present embodiment, only the inner side one (B1, C3 in the example illustrated in FIG. 2) of the arc curves is a detection target, and the outer side one (B2) of the arc curves is not a detection target. This is because, in the arc curve B2, the inner side and the outer side of the arc curve respectively correspond to a high-luminance region corresponding to the film and an object with a relatively low luminance different from the bubble, so that the luminance changes to decrease in the direction from the inner side toward the outer side of the arc curve. This configuration will not be disadvantageous because the bubble can be sufficiently detected as long as the inner arc curve is detected.

Figure 4:
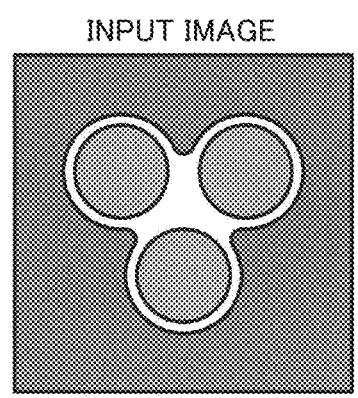
FIG. 4 illustrates an example of an arc curve in a case where a plurality of bubbles are densely arranged.

When a plurality of bubbles are densely arranged as illustrated in FIG. 4, the bubbles may be attached to each other to render the monitoring of the outer arc curve difficult. For example, in FIG. 4, an upper left bubble has the outer arc curve lacking a lower right portion due to contact with another film. The process can be performed in the situation illustrated in FIG. 4 without any problem because the outer arc curve is not a detection target as described above. The present applicant has made research to find out that the inner arc curves are likely to be monitorable even in the densely arranged state. Thus, with the method according to the present embodiment, the bubble region can be extracted no matter how densely the bubbles are arranged.

The input image according to the present embodiment may in particular be an in-vivo image. In this case, the processing section 100 performs a process of detecting a region of interest from a region as a result of excluding the extracted bubble region from the in-vivo image, for example.

In many cases, an in-vivo image, which is an image of the inside of a living body, includes bubbles, which might hide an object of interest such as a lesioned part. Thus, a calculation load can be reduced to achieve an efficient process, with the bubble region excluded from the process of detecting the region of interest. Here, the region of interest is a region in which the object of interest described above has been imaged, specifically a lesion area. The bubble region might also be erroneously detected as the region of interest (lesion area), and thus higher process accuracy can be achieved with the bubble region excluded from the process of detecting the region of interest. In any case, the in-vivo image benefits more and thus is more positively impacted when the method according to the present embodiment including the process of extracting the bubble region is applied, than general images such as a portrait.

Note that the input image according to the present embodiment includes various types of images that may include bubbles. For example, the input image includes: a captured image of a liquid such as a medicine or an industrial machine that might be affected by bubbles produced (attached) thereon; and an image captured in a sprayed environment where bubbles are supposed to be sprayed (when fire foam is sprayed, for example).

The method according to the present embodiment is described in detail below. Specifically, a system configuration example of an image processing device or the like is described first, and then a flow of a process is described with reference to a flowchart or the like.

2. System Configuration Example

Figure 5:
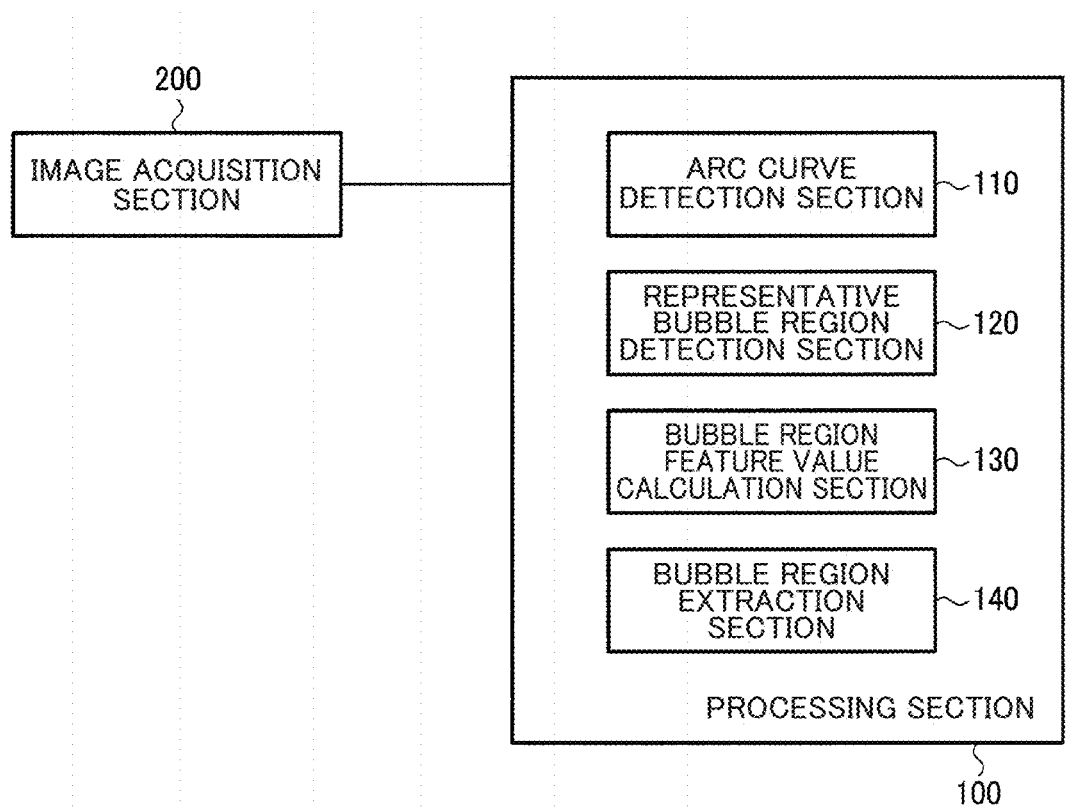
FIG. 5 illustrates a detailed configuration example of the image processing device according to the present embodiment.

FIG. 5 illustrates a system configuration example of an image processing device according to the present embodiment. The image processing device includes the image acquisition section 200 and the processing section 100. The processing section 100 includes an arc curve detection section 110, a representative bubble region detection section 120, a bubble region feature value calculation section 130, and a bubble region extraction section 140. Note that the image processing device is not limited to the configuration illustrated in FIG. 5, and may be modified in various ways with some of the components omitted or other components added.

The image acquisition section 200 acquires an input image. For example, this input image might include bubbles as illustrated in FIG. 6A.

The arc curve detection section 110 detects an arc curve from the input image. For example, a method according to Viorica Patraucean et al.,1 may be employed for the detection. In such a case, arc curves detected by the arc curve detection section 110 have somewhat similar gradient directions on the arc curves. FIG. 6B illustrates an example of a result of detecting an arc curve in the input image illustrated in FIG. 6A. FIG. 6B illustrates an example of a result of directly applying the method according to Viorica Patraucean et al.,1, and thus, not only the arc curve but also line segments are detected.

The representative bubble region detection section 120 detects a region that is likely to be a bubble region as a representative bubble region, based on the arc curve thus detected. The representative bubble region is detected with an arc curve that is likely to correspond to a bubble selected from the arc curves detected in FIG. 6B. Specifically, the arc curve involving a change in the pixel luminance increasing in a direction from the inner side toward the outer side of the arc curve as described above may be selected. More specifically, a similarity between a gradient direction and a direction away from the center of the pixel value on the arc curve may be determined as will be described in detail later. For example, the representative bubble region detected is white regions illustrated in FIG. 6C.

The bubble region feature value calculation section 130 obtains a bubble region feature value serving as a feature value of a bubble region, based on information on pixels in the representative bubble region.

The bubble region extraction section 140 extracts a bubble region from the input image based on the bubble region feature value. If the entire process performed by the image processing device according to the present embodiment is defined as a bubble region extraction process in a broad sense, the process performed by the bubble region extraction section 140 is a bubble region extraction process in a narrow sense. The bubble region extraction process in a narrow sense is a process of obtaining a bubble region by expanding a representative bubble region, and corresponds to a process of obtaining what is illustrated in FIG. 6D from what is illustrated in FIG. 6C. For example, a graph cut process may be employed as will be described in detail later.

The method according to the present embodiment is not limited to a method applied to an image processing device, and may be applied to an endoscope apparatus for example. An endoscope apparatus (endoscope system) according to the present embodiment is described with reference to FIG. 7. The endoscope apparatus according to the present embodiment includes a rigid scope 10 that is inserted into a body, an imaging section 20 that is connected to the rigid scope 10, a processing device 30, a display section 40, an external I/F section 50, and a light source section 60.

The light source section 60 includes a white light source 61 that emits white light, and a light guide cable 62 that guides the light emitted from the white light source 61 to the rigid scope.

The rigid scope 10 includes a lens system 11 that includes an objective lens, a relay lens, an eyepiece, and the like, and a light guide section 12 that guides the light emitted from the light guide cable 62 to the end of the rigid scope.

The imaging section 20 includes an imaging lens system 24 that forms an image of the light emitted from the lens system 11. The imaging lens system 24 includes a focus lens 22 that adjusts the in-focus object position. The imaging section 20 also includes an image sensor 25 that photoelectrically converts the reflected light focused by the imaging lens system 24 to generate an image, a focus lens driver section 23 that drives the focus lens 22, and an autofocus (AF) start/stop button 21 that controls AF start/stop.

The image sensor 25 is a primary color Bayer image sensor in which any of R, G, and B color filters are disposed in a Bayer array, for example. Alternatively, an image sensor that utilizes a complementary color filter, a stacked image sensor that is designed so that each pixel can receive light having a different wavelength without using a color filter, and a monochrome image sensor that does not utilize a color filter may be employed as long as the object can be captured to obtain an image. The focus lens driver section 23 is implemented by any desired actuator such as a voice coil motor (VCM), for example.

The processing device 30 corresponds to the image processing device described above, and includes an image acquisition section 31 (corresponding to the image acquisition section 200) and a processing section 32 (corresponding to the processing section 100) as described above with reference to FIG. 3.

The image acquisition section 31 acquires an image captured by the imaging section 20, as an input image. The captured image thus acquired is temporary continuous (time-series) images in a narrow sense. For example, the image acquisition section 31 may be an A/D conversion section. The A/D conversion section performs a process of converting analog signals sequentially output from the image sensor 25 into a digital image. The image acquisition section 31 (or an unillustrated pre-processing section) may perform pre-processing on the captured image. For example, the pre-processing is image processing including a white balance process and an interpolation process (demosaicing process).

The processing section 32 has a configuration similar to that in FIG. 5, and performs the bubble region extraction process in a broad sense. As described above, the processing section 32 may perform a process of detecting a region of interest from a region in an in-vivo image excluding the extracted bubble region. The processing section 32 may perform other processes such as AF control. For example, the processing device 30 (control device, control section) is mutually connected with and exchanges control signals with the external I/F section 50, the image sensor 25, the AF start/end button 21, and the light source section 60. The external I/F section 50 is an interface that allows the user to perform an input operation on the endoscope apparatus, for example. For example, the external I/F section 50 includes a setting button for setting the position and the size of the AF area, an adjustment button for adjusting image processing parameters, and the like.

The display section 40 is a liquid crystal monitor, for example. The display section 40 displays images sequentially output from the processing section 32.

Figure 7:
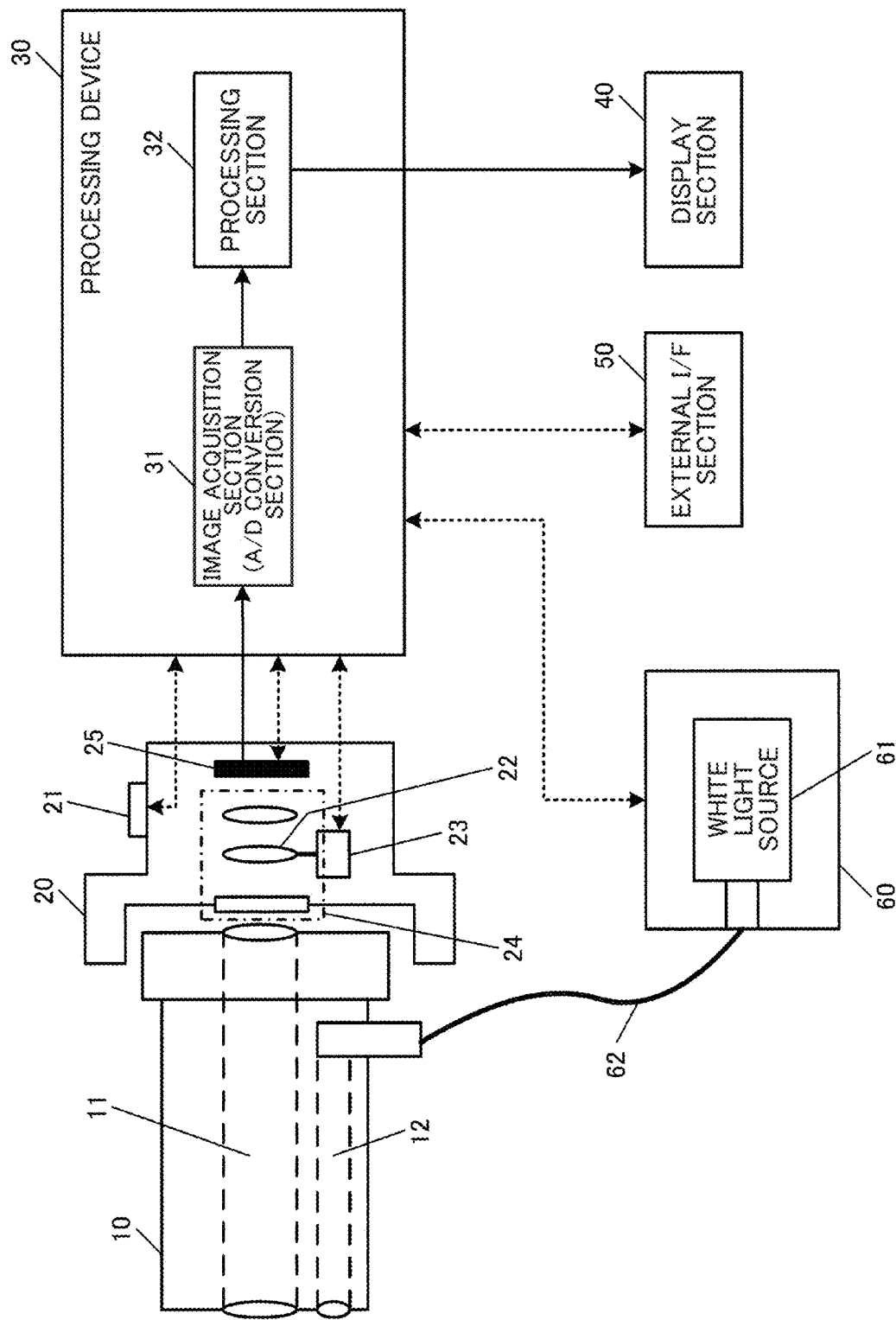
FIG. 7 illustrates a configuration example of an endoscope apparatus according to the present embodiment.

FIG. 7 illustrates an example of a rigid scope used for laparoscopic surgery or the like. The present embodiment is not limited to the endoscope apparatus with this configuration. The present embodiment may be applied to other endoscope apparatuses such as an upper endoscope and a lower endoscope. The endoscope apparatus is not limited to the configuration illustrated in FIG. 7. The configuration may be modified in various ways with the components partially omitted, or additional components provided. For example, the endoscope apparatus illustrated in FIG. 7 is supposed to perform AF and thus includes the focus lens 22 and the like. Alternatively, the endoscope apparatus according to the present embodiment may have a configuration of not performing AF. In such a configuration, the components for AF may be omitted

3. Process Details

Figure 8:
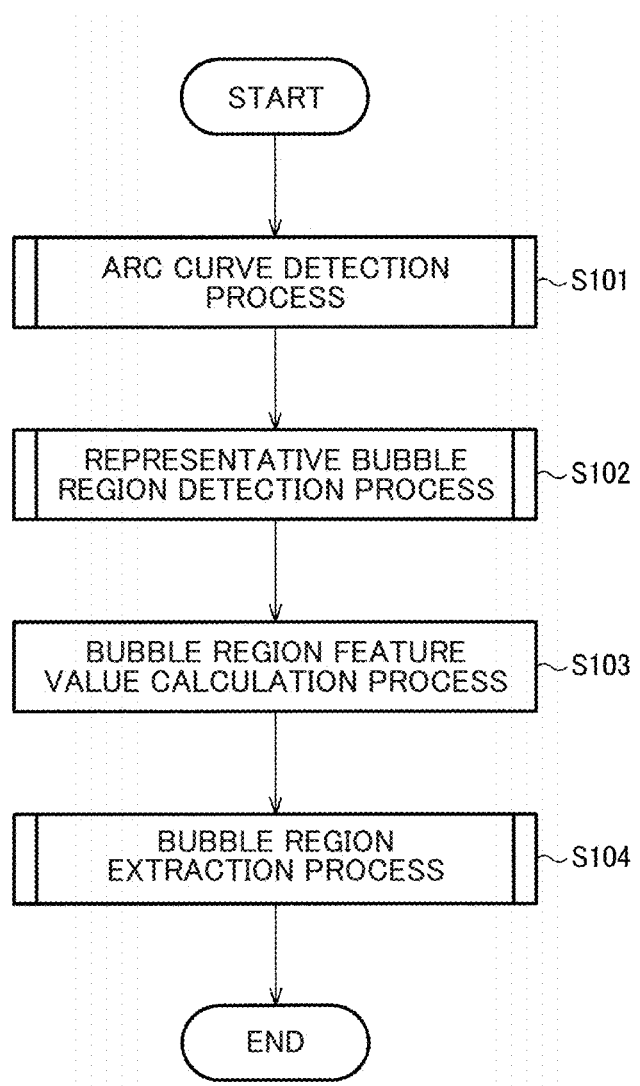
FIG. 8 is a flowchart illustrating a process according to the present embodiment.

FIG. 8 is a flowchart illustrating a process according to the present embodiment. A process performed by each section of the image processing device is described in detail with reference to the flowchart.

It is assumed that the process of acquiring an input image by the image acquisition section 200 has been completed before the process illustrated in FIG. 8 starts. For example, this input image is a 3-channel (RGB) image, and a description is given below with the 3-channel (RGB) image as an example. Note that a modification employing a 1-channel (Gray) image or an image defined in another color space as an input image may be implemented.

The arc curve detection section 110 detects an arc curve from the input image (S101). A flow of the arc curve detection process is described in detail with reference to a flowchart in FIG. 9. When the arc curve detection process starts, first of all, a similar gradient direction region is detected (S201). The gradient direction is a direction indicating a gradient or change in a pixel value, and is information that can be defined for each pixel of the input image. The direction may be obtained through a method illustrated in FIG. 10.

When the input image is the 3-channel (RGB) image, each pixel has three pixel values RGB. In this example, a luminance value is obtained based on the three pixel values RGB, and the pixel value gradient direction may be obtained as a direction indicating a gradient and change in the luminance value. Alternatively, the 3-channel (RGB) image may be converted into a 1-channel (Gray) image, and the pixel value gradient direction may be obtained as a direction indicating a gradient and change in the pixel value in the image after the conversion. Alternatively, the gradient direction may be obtained based on any one of the pixel values RGB, or may be obtained based on a combined pixel value obtained with any two of the pixel values RGB. Alternatively, the gradient direction may be obtained based on a combination of the three pixel values RGB combined with a combination ratio different from that for obtaining a general luminance value Y. Thus, the pixel value gradient direction according to the present embodiment is a direction indicating a gradient and change in pixel value information based on the pixel value of each pixel in a broad sense, and the pixel value information includes various types of information such as a luminance value as described above. In the example descried below, the luminance value is used.

Figure 10:
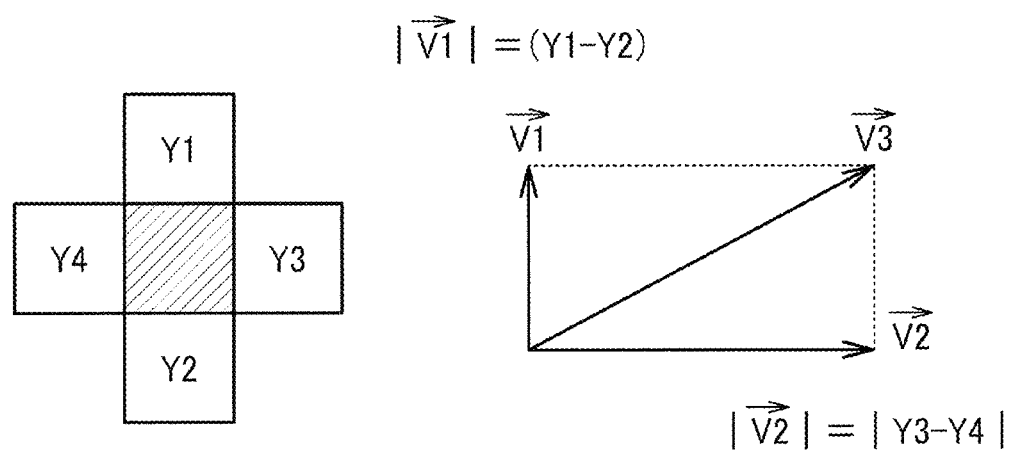
FIG. 10 is a diagram illustrating a method of obtaining a gradient direction at a given pixel.

First of all, as illustrated in FIG. 10, a gradient in the vertical direction and a gradient in the horizontal direction are obtained for a process target pixel. For example, the gradient in the vertical direction may be obtained with a difference value indicating a difference in the luminance value between pixels immediately above and below the process target pixel. The gradient direction in the vertical direction is a direction in which the luminance value increases, and is defined by positive/negative of the difference value. For example, the gradient direction is an upward direction when a positive value is obtained as a result of subtracting the luminance value of the pixel immediately below from the luminance value of the pixel immediately above, and is a downward direction when a negative value is obtained as a result of subtracting the luminance value of the pixel immediately below from the luminance value of the pixel immediately above. A gradient magnitude in the vertical direction is obtained with an absolute value of the difference value. Thus, the gradient may be regarded as a vector with a direction indicating the gradient direction and a magnitude indicating the gradient magnitude. Similarly, a vector representing the gradient in the horizontal direction is obtained based on a difference value indicating a difference in the luminance value between pixels on the immediately on the right and left sides of the process target pixel, for example.

The gradient direction at the process target pixel may be a direction of a synthetic vector obtained with the vector indicating a gradient in the vertical direction and the vector indicating a gradient in the horizontal direction. In the example illustrated in FIG. 10, the gradient direction at the process target pixel is a direction of a synthetic vector V3 obtained with a vector V1 indicating a gradient in the vertical direction and a vector V2 indicating a gradient in the horizontal direction. The gradient direction may be obtained with the following Formula (1). In the following Formula (1), Y1 represents the luminance value of the pixel immediately above the process target pixel, Y2 represents the luminance value of the pixel immediately below the process target pixel, Y3 represents the luminance value of the pixel immediately on the right side of the process target pixel, Y4 represents the luminance value of the pixel immediately on the left side of the process target pixel, and θ represents an angle indicating the gradient direction with a counterclockwise direction from the right direction defined as a positive direction. In FIG. 10, the gradient direction is obtained from the two directions of the vertical direction and the horizontal direction. Alternatively, the gradient direction may be obtained also based on diagonal directions by using eight surrounding pixels. Thus, the process of calculating the gradient direction may be modified in various ways.

[Formula 1]

$$\theta = \tan^{-1} \frac{(Y1 - Y2)}{(Y3 - Y4)} \quad (1)$$

Figure 11A:
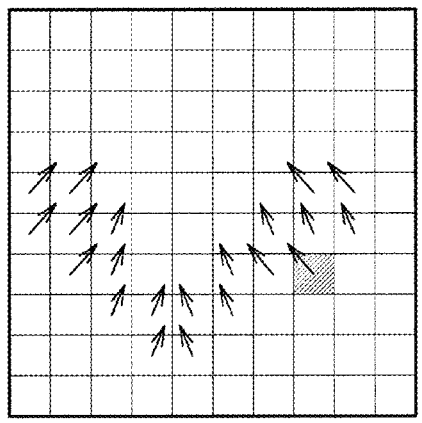
FIG. 11A and FIG. 11B is a diagram illustrating a process of detecting a similar gradient direction region.
Figure 11B:
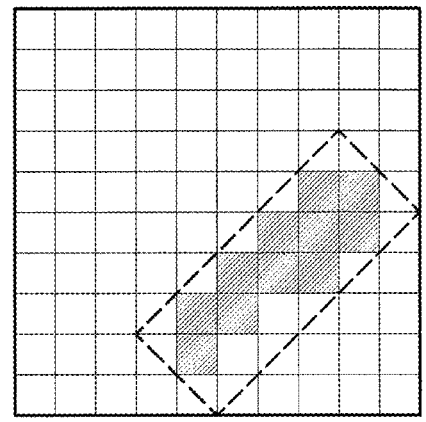

In the process of detecting the similar gradient direction region (S201), the similar gradient direction region is obtained by combining a plurality of pixels with similar gradient directions, based on the gradient directions obtained for the pixels. For example, the process may be performed in such a manner that when neighborhood pixels of a given pixel, serving as a base point, have similar gradient directions, the similar gradient direction region including the neighborhood pixels is obtained. FIG. 11A and FIG. 11B schematically illustrate the process of detecting the similar gradient direction region. FIG. 11A illustrates an example of gradient directions at pixels. In this figure, pixels with a gradient magnitude not larger than a predetermined value are omitted. When the base point is a hatched pixel in FIG. 11A, hatched pixels in FIG. 11B are combined to the pixel, and the similar gradient direction region is a region defined by the broken line in FIG. 11B. As illustrated in FIG. 11B, the pixels in a single similar gradient direction region have similar gradient directions.

Figure 12:
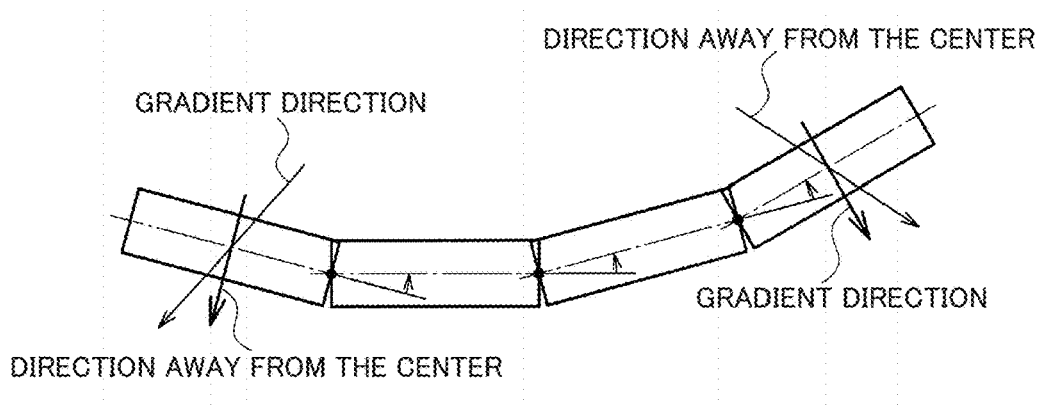
FIG. 12 is a diagram illustrating a process of combining the similar gradient direction regions.

Then, adjacent similar gradient direction regions are joined to each other (S202). In this process, whether or not the adjacent similar gradient direction regions are joined to form a smooth curve shape as illustrated in FIG. 12 is determined. The adjacent similar gradient direction regions determined to form a smooth curve are joined. For example, a direction of each similar gradient direction region may be obtained. Then, two similar gradient direction regions with directions defining an angle within a given angle range (an angle range with which a smooth curve can be formed) may be joined to each other. When the similar gradient direction region has a rectangular form as illustrated in FIG. 11B, the direction of the similar gradient direction region may be a longitudinal direction of the rectangular form.

The condition for joining is not limited to the joining to form a smooth curve, and may include joining of adjacent similar gradient direction regions with gradient directions having a high similarity. For example, a representative gradient direction of each similar gradient direction region may be obtained. Then, two similar gradient direction regions with a representative gradient direction defining an angle within a given angle range may be joined to each other. The representative gradient direction may be determined by averaging gradient directions at all the pixels in the similar gradient direction region as described above, for example. Alternatively, the representative gradient direction may be a gradient direction at a given pixel in the similar gradient direction region, because the pixels in the similar gradient direction region have similar gradient directions as described above.

The similar gradient direction regions, joined to each other in S202, are approximated by an arc curve (S203). Thus, a single arc curve is detected. For example, the processes in S201 to S203 can be implemented by the method in Viorica Patraucean et al.,1. Through the processes described above, an arc curve is detected from an input image. This single arc curve is defined with pixels on the arc curve having similar gradient directions.

Figure 9:
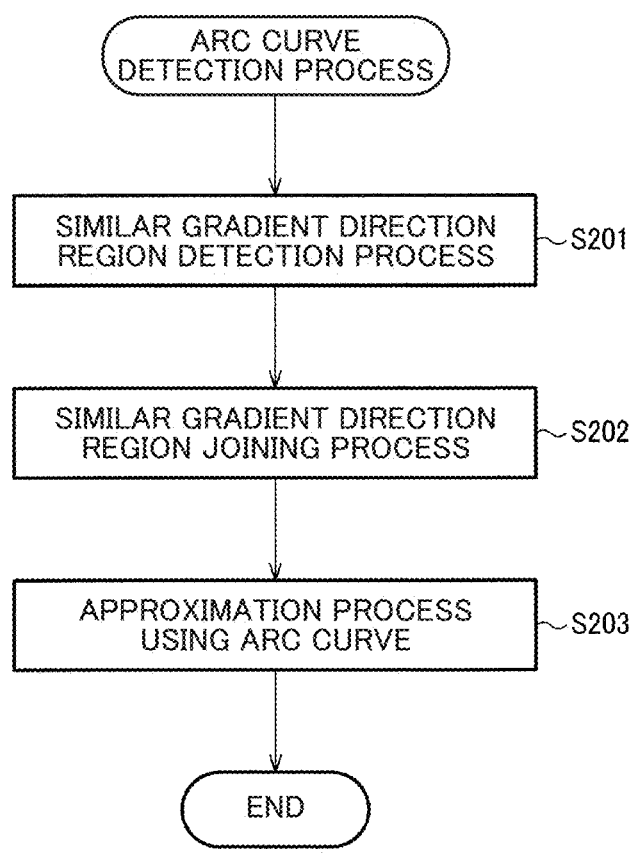
FIG. 9 is a flowchart illustrating an arc curve detection process.

The arc curve detection process in S101 is not limited to the process illustrated in FIG. 9, and other modifications may be employed. For example, an arc curve may be detected through Hough transform or the like. In this configuration, only the arc curve defined with the same gradient direction of the pixel values may be detected, or arc curves not satisfying this condition may be also detected but then discarded.

Then, the representative bubble region detection section 120 may detect a representative bubble region that is likely to be a bubble region based on the arc curves detected in S101 (S102). Note that the arc curve, among the arc curves detected in S101, satisfying a given condition needs to be detected in S102.

Specifically, the arc curves detected in the process in S101 have somewhat similar gradient directions. In this process, the relationship between this direction and the portions on the inner and the outer sides of the arc curves is not taken into consideration yet. The arc curve to be detected in the present embodiment involves a change in the pixel luminance increasing in the direction from the inner side toward the outer side of the arc curve. Thus, if the gradient direction is defined as a direction in which the luminance value increases as described above, that is, a direction in which the brightness indicated by the luminance changes to increase, the representative bubble region is detected with the gradient direction in a direction from the inner side toward the outer side of the arc curve.

Figure 13:
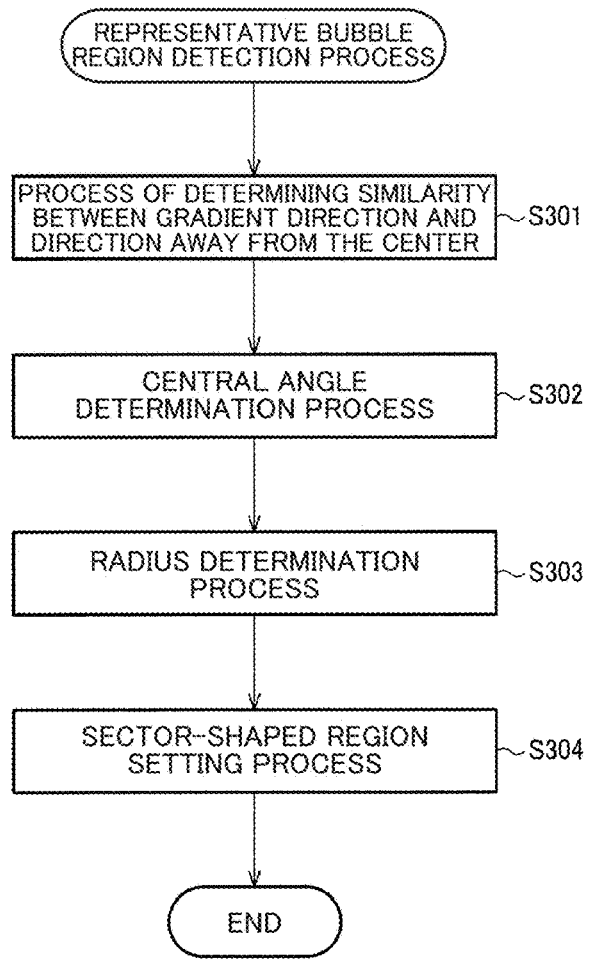
FIG. 13 is a flowchart illustrating a representative bubble region detection process.

FIG. 13 is a flowchart illustrating a representative bubble region detection process. In the representative bubble region detection process, a similarity between the gradient direction of the arc curve detected in S101 and a direction away from the center is determined (S301). Thus, an arc curve with a high similarity is a detection target, and an arc curve with a low similarity is excluded (discarded). The direction away from the center is a direction from the inner side toward the outer side of the circular shape defined by the arc curve, and is specifically a direction of getting away from the center. Thus, for example, the center of the circular shape defined by the arc curve may be obtained, and the direction away from the center at a given pixel on the arc curve may be obtained as a direction from the center toward the pixel. Note that the direction away from the center may be any direction from the inner side toward the outer side of the circular shape, and is not limited to a direction based on the center of the circle or the focal point or the center of gravity of an ellipse.

For example, a process of determining the similarity between the gradient direction and the direction away from the center may be performed with an inner product of vectors indicating two directions. Specifically, the similarity may be determined to be high when the inner product is a positive value, and is determined to be low when the similarity is 0 or less. This can be regarded as a process of determining that the similarity is high when the difference between the gradient direction and the direction away from the center is smaller than 90°. Alternatively, a specific angle between two directions may be obtained, and compared with a given angle threshold value. The similarity between the two directions can be more precisely determined with a smaller angle threshold value.

Through the process described above, an arc curve involving a change in the pixel luminance increasing in the direction from the inner side toward the outer side is detected from the input image.

Figure 14:
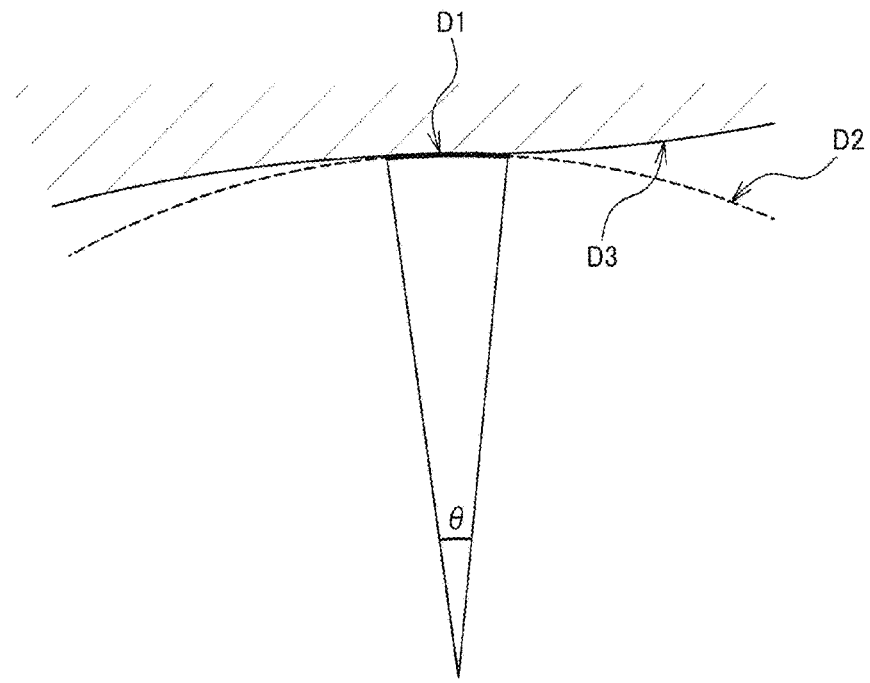
FIG. 14 is a diagram illustrating how an arc curve with a small central angle is excluded.

In the present embodiment, the arc curve used for the representative bubble region detection process may be limited with further conditions. Specifically, a central angle of the arc curve is obtained to determine whether or not this central angle $\theta$ is equal to or larger than a predetermined threshold value $\kappa\_\theta$, and the arc curve with the central angle that is equal to or larger than the threshold value is used (S302). The arc curve with a small central angle has a small curvature (large radius of curvature) as illustrated in FIG. 14. In this configuration, the arc curve D1 detected might not be a part of the circular shape (D2) and might be a part of a shape (D3) different from the circular shape. This D3 clearly corresponds to a structure different from the bubble region. Thus, with an arc curve with an excessively small central angle excluded, the risk of erroneously detecting a non-bubble structure, such as D3, as a bubble can be reduced.

In the representative bubble region detection process, whether or not a radius r of an arc curve is within a predetermined range (for example, equal to or larger than κ_r1 and equal to or smaller than κ_r2) may be determined, and an arc curve with the radius r included in the range may be used (S303). Thus, an arc curve with an excessively small or large radius can be excluded from the process.

The arc curve with an excessively small radius is an arc curve that is accidentally detected and thus is less likely to be a bubble. When the radius of a bubble is large, a target object may be observable through the bubble, and thus the bubble may be preferably not detected as a bubble. Thus, with the range of the radius r limited, the arc curve that needs to be used as the bubble can be detected, whereby high detection accuracy can be achieved.

Through S301 to S303, an appropriate one of the arc curves, detected in S101, is selected (employed), and a region formed of the selected arc curve is set as the representative bubble region. The region formed of an arc curve includes various forms. For example, a sector-shaped region with the arc curve serving as an arch may be used (S304).

In the example illustrated in FIG. 13, S301 to S303 are performed in the order described above. Alternatively, the order of the processes may be changed. Furthermore, a modification where the processes in S302 and S303 are omitted may be implemented. Through the processes described above, as illustrated in FIG. 6C, regions in the input image that are likely to be bubble regions can be detected as representative bubble regions.

Next, the bubble region feature value calculation section 130 calculates a feature value distribution for the pixels in the representative bubble region, as a bubble region feature value (S103). The feature value, which may be of various values, may be a five-dimensional feature value based on coordinates (x, y) of each pixel and the pixel values of the colors (R, G, B), for example. As can be seen in FIG. 6C, the representative bubble region is expected to be a region including a plurality of pixels, and the five-dimensional feature value is obtained from each of the pixels, whereby each of the elements (x, y, R, G, B) of the feature value fluctuates within a certain range. Thus, in the present embodiment, the fluctuations of the feature value (distribution) are approximated by a given model.

For example, the distribution of the feature quantities may be approximated with a Gaussian mixture model. The input image may include bubbles at two or more separate portions. Thus, the distribution of (x, y) has a plurality of peaks. The color of the bubbles may change in accordance with a situation (for example, in accordance with a portion that is an imaging target in an in-vivo image), and thus might result in a distribution having a plurality of peaks. Even in such a case, the Gaussian mixture model can be used for accurate approximation.

Still, how the distribution of the feature value is expressed is not limited to the approximation using the Gaussian mixture model. For example, the distribution of the feature value may be expressed with a histogram.

Next, the bubble region extraction section 140 extracts a bubble region based on the bubble region feature value obtained from the representative bubble region (S104). The bubble region may be extracted by the graph cut process for example, which is a technique used for extracting a region from an image or for other like purposes. Specifically, the entire image is expressed with a graph structure, with energy based on information on a color distribution and an edge of the image. Then, this graph is solved as a max flow problem, so that binary mask images can be obtained with labels 0 and 1 assigned to achieve minimum possible energy.

Figure 15:
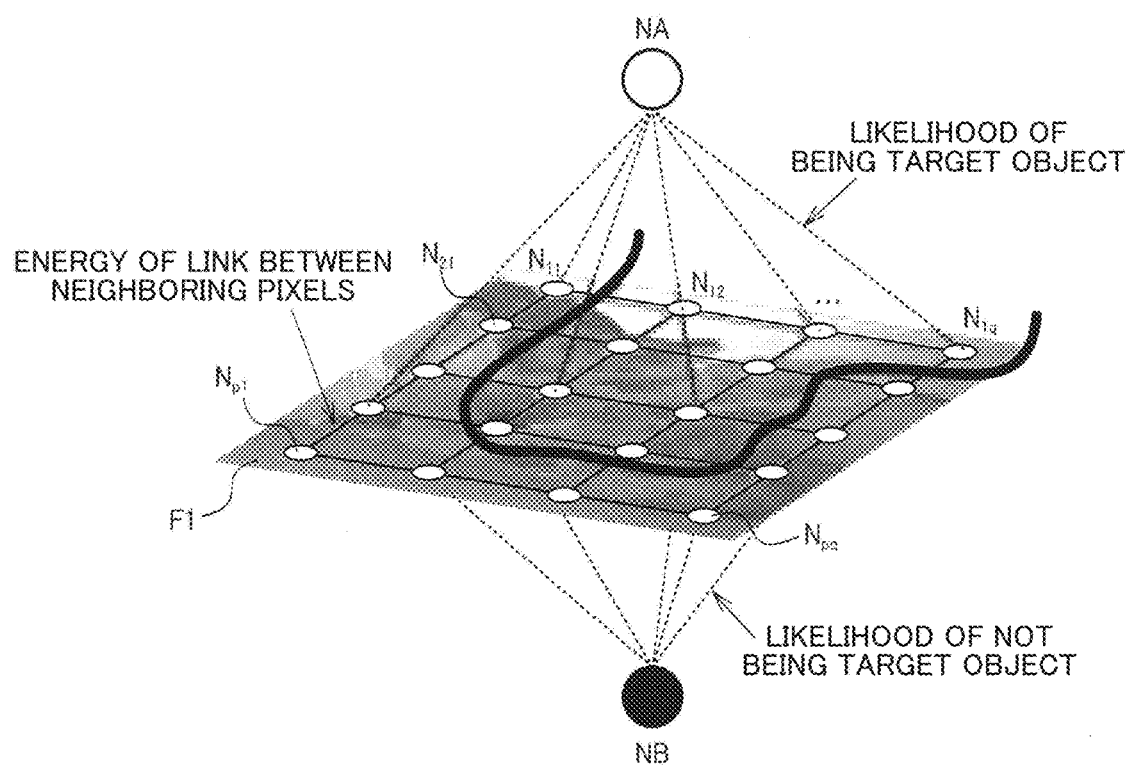
FIG. 15 is a schematic view illustrating a graph cut process.

FIG. 15 is a schematic view illustrating a process of the graph cut process. For example, a node NA and a node NB, on upper and lower sides in FIG. 15, respectively represent a bubble region and a non-bubble region. A plane F1 corresponds to an input image. Nodes $N_{11}$ to $N_{pq}$ on F1 (an input image with p pixels×q pixels, for example) each represent a pixel in the input image. A link establishes connection between NA and each of the nodes $N_{11}$ to $N_{pq}$, between NB and each of the nodes $N_{11}$ to $N_{pq}$, and between two nodes, in $N_{11}$ to $N_{pq}$, corresponding to adjacent pixels. Energy is set as a weight to each link.

In an example of a graph as illustrated in FIG. 15, the graph is segmented into a region connected to the node NA and a region connected to the node NB. A node (pixel) connected to the node NA after the segmentation is determined to be a bubble region, and a node (pixel) connected to the node NB after the segmentation is determined to be a non-bubble region. The graph cut process searches for cut (min cut) requiring a minimum cost (energy).

Specifically, the following process is performed for connection between each of the adjacent pixels in the input image. First of all, inter-adjacent pixel energy E_edge is calculated. This is energy provided to a link between a node representing a given pixel and a node representing a pixel neighboring the pixel. For example, the inter-adjacent pixel energy E_edge may be obtained by E_edge=exp(−D_frame), where D_frame represents a Euclid distance between pixel values of adjacent pixels in an RGB color space. Thus, closer colors lead to a larger energy, and thus a link between pixels with close colors is less likely to be cut, whereby pixels with similar colors are likely to be determined to be in the same region.

Figure 16:
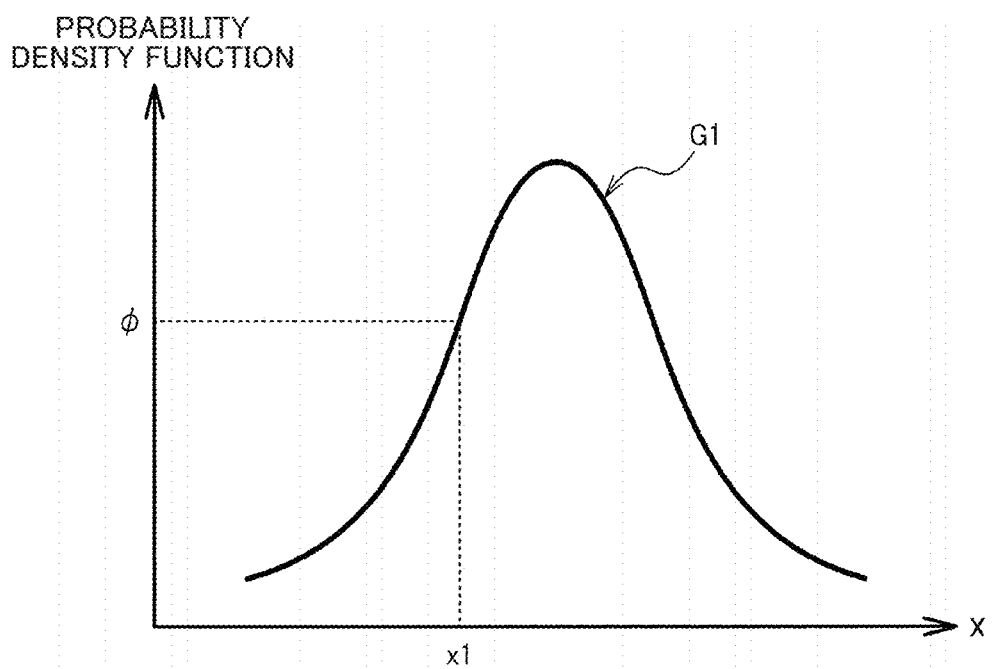
FIG. 16 is a diagram illustrating a method of obtaining a similarity from a bubble region feature value (distribution).

Foreground likelihood energy and background likelihood energy are calculated for each pixel in the input image, in a manner described below. The foreground likelihood energy E_f is provided to a link between the node NA representing a bubble region and each of the nodes $N_{11}$ to $N_{pq}$. The foreground likelihood energy E_f may be a similarity between the feature value of a target pixel (the coordinates and the pixel values of the pixel) and the bubble region feature value described above. For example, the bubble feature value may be approximated by a distribution G1 in FIG. 16. FIG. 16 illustrates an example of a one-dimensional feature value with the approximated distribution being the simplest Gaussian distribution, for simplifying the description. When a feature value x' of a pixel is a value illustrated in FIG. 16, the similarity (foreground likelihood energy) between the feature value of the pixel and the bubble region feature value may be φ or a value based on φ. Thus, when a similarity between the feature value and the bubble region feature value is high, high energy is provided, whereby a link between the pixel and NA is less likely to be cut and the pixel is likely to be determined to be in the bubble region.

The background likelihood energy E_b is defined by E_b=κ (κ is a predetermined value). If a region that is unlikely to be a bubble region has been detected in the input image, E_b may be a similarity between the feature value based on the region and the feature value of each pixel, as in the case of E_f. However, only "representative bubble region" (a region that is likely to be the bubble region) and "the other regions" are detected in the process according to the present embodiment (S101 to S103). The region other than the representative bubble region might include a region that is actually a bubble, and thus the feature value obtained from the region other than the representative bubble region is unsuitable for being used as the "non-bubble feature value". Thus, in the present embodiment, a given fixed value is used for the background likelihood energy representing the likelihood to be the background (likelihood of not being the bubble region).

Figure 17:
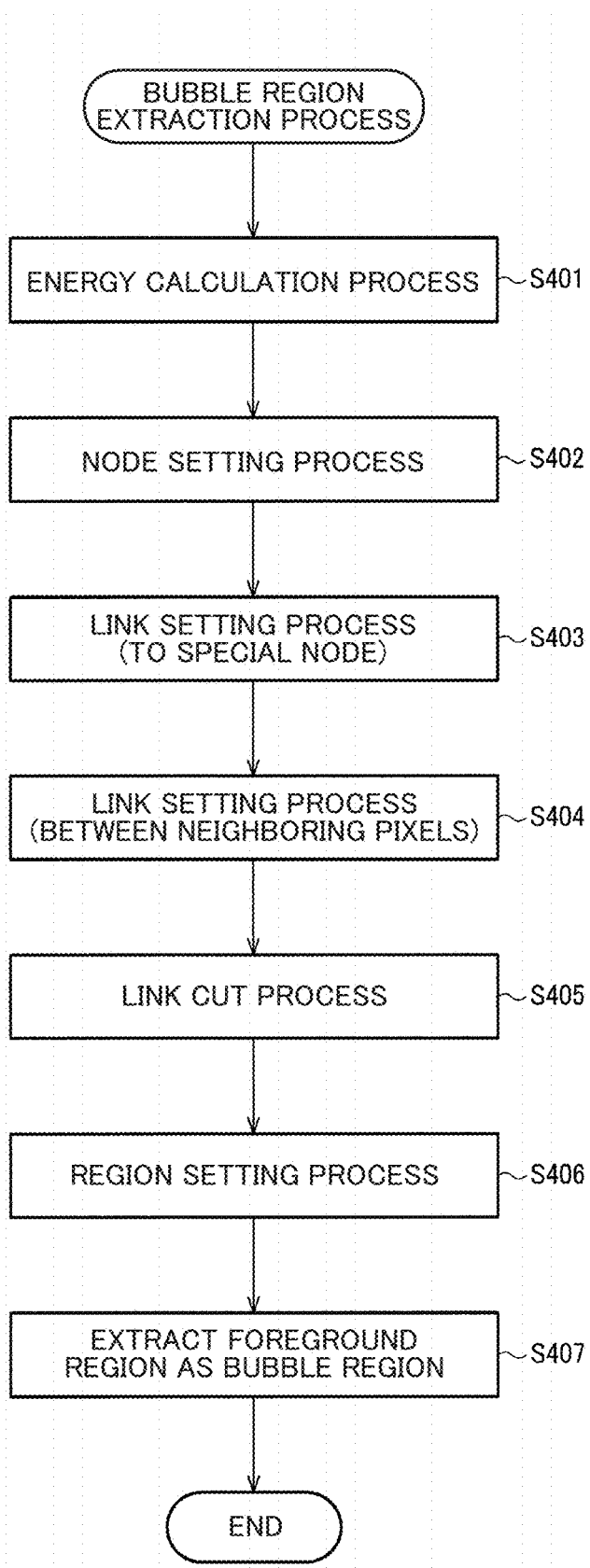
FIG. 17 is a flowchart illustrating a bubble region extraction process.

Through the process described above, the graph and the energy between nodes are obtained. Thus, the graph cut process is applied to the input image based on the inter-adjacent pixel energy, the foreground likelihood energy, and the background likelihood energy for segmentation into a foreground region (bubble region) and a background region (non-bubble region). For example, FIG. 17 is a flowchart illustrating a specific procedure of the bubble region extraction process using the graph cut process, which may be performed in various possible ways.

When this process starts, first of all, an energy calculation process is performed (S401). Specifically, the process of obtaining the inter-adjacent pixel energy E_edge, the foreground likelihood energy E_f, and the background likelihood energy E_b described above is performed.

Next, a node setting process is performed (S402). Specifically, each pixel in the input image is set as a node. Furthermore, a source node (corresponding to NA) and a sink node (corresponding to NB) are added as special nodes representing the foreground region and the background region.

Next, a process of setting a link for establishing connection with the special node is performed (S403). Specifically, a link establishing connection between the source node and each pixel is set, and the foreground likelihood energy E_f, obtained in S401, is set as a weight to the link. Similarly, a link establishing connection between the sink node and each pixel is set, and the background likelihood energy E_b, obtained in S401, is set as a weight to the link.

Then, a process of setting a link between neighborhood nodes is performed (S404). Specifically, a link is set between each pixel and a adjacent pixel, and the inter-adjacent pixel energy, obtained in S401, is set as a weight to the link.

Through the process described above, the graph is set. Then, the links are cut in such a manner that a group of nodes connected to the source node and a group of nodes connected to the sink node are completely separated from each other (S405). In this process, a set of links are cut with the minimum sum of the weights set to the links to be cut. This set of links is calculated by the graph cut process.

When the min cut is found, the foreground region (bubble region) and the background region (non-bubble region) are set based on the min cut thus found (S406). Specifically, in a state after the cut, a group of nodes connected to the source node and a group of nodes connected to the sink node are respectively set as the foreground region and the background region.

In the present embodiment for extracting the bubble region, the foreground region, as one of the segmented regions, is extracted as the bubble region (S407).

The process (process in S104) of extracting the bubble region based on the bubble region feature value is not limited to the graph cut process. For example, a similarity between the feature value of each pixel in the input image and the bubble region feature value may be obtained, and a group of pixels with the similarity exceeding the predetermined threshold value κ_s may be simply extracted as the bubble region.

With the method according to the present embodiment, a bubble region can be extracted from an image while reducing a risk of erroneously extracting a non-bubble region.

In the present embodiment, the processing section 100 (in a narrow sense, the representative bubble region detection section 120) determines the similarity between the gradient direction of a pixel value on the arc curve and a direction away from the center of the arc curve. When the similarity is high, a change in the luminance increasing in a direction from the inner side toward the outer side of the arc curve is determined to be occurring.

As described above with reference to FIG. 10, the gradient direction is information indicating the direction in which the luminance changes. The direction away from the center is a direction from the inner side toward the outer side of the arc curve. In a narrow sense, the direction away from the center of a target pixel on the arc curve is a direction from the center of a circle defined by the arc curve (the arc curve being a part of the circle) toward the target pixel.

Thus, with the configuration where two directions are defined, whether or not the change in the luminance increasing in the direction from the inner side toward the outer side of the arc curve is occurring, that is, whether or not the target arc curve corresponds to a bubble can be determined, based on the similarity between the directions. The similarity may be determined based on whether or not the inner product is a positive or negative value, or may be determined by the process of comparing an angle between the two directions and a given threshold value.

The processing section 100 (in a narrow sense, the arc curve detection section 110) may detect an arc curve by combining a plurality of pixels determined to have similar gradient directions.

As described above with reference to FIG. 10, the gradient direction is obtained for each pixel in this example. Thus, whether or not the pixels are similar to each other in the gradient direction can be determined in the following manner. Specifically, the gradient direction is obtained for each of two target pixels, and the pixels may be determined to be similar to each other if the difference between the gradient directions is small. More specifically, an angle between the two gradient directions may be obtained, and the gradient directions may be determined to be similar to each other if the angle is small (for example, equal to or smaller than a given threshold value).

Thus, as illustrated in FIG. 11A and FIG. 11B, the arc curve can be detected as a group of pixels with similar gradient directions (similar gradient direction region). As described above, pixels in a similar gradient direction region have similar gradient directions, and thus a certain level of similarity between the gradient direction and the direction away from the center is achieved at any of the pixels in the similar gradient direction region.

Thus, the processing section 100 (in a narrow sense, the representative bubble region detection section 120) can determine whether or not the change in the luminance increasing in the direction from the inner side toward the outer side of the arc curve is occurring, by determining the similarity between the gradient direction of the target pixel in the arc curve and the direction away from the center at the target pixel.

Thus, in the present embodiment, whether or not the arc curve corresponds to a bubble is determined based on the similarity between the gradient direction and the direction away from the center. If the relationship between the gradient direction and the direction away from the center is similar among all the pixels in the similar gradient direction region, the similarity between the gradient direction and the direction away from the center may be determined for only a small number of points (a single point in a narrow sense) in a single similar gradient direction region. Thus, the processing load for determining the similarity between the gradient direction and the direction away from the center can be reduced. Thus, in this example, a single target pixel may be set for each of a plurality of similar gradient direction regions corresponding to a single arc curve, for example.

As described above, the similar gradient direction regions may be joined to each other under the conditions that the adjacent similar gradient direction regions form a smooth curve, and that the change in the representative gradient direction is not so large (the latter condition is not a requirement). Thus, when three or more similar gradient direction regions are joined to each other as illustrated in FIG. 12, the absolute gradient direction might not match among the similar gradient direction regions, but a relationship between the gradient directions of the similar gradient direction regions and the direction from the inner side toward the outer side of the smooth curve (that is, the arc curve) is expected to be similar over the entire target arc curve.

In the example illustrated in FIG. 12, the representative gradient direction of the similar gradient direction region on the right side is a lower right direction, whereas the representative gradient direction of the similar gradient direction region on the left side is a lower left direction. Still, the relationship that "the similarity between the gradient direction and the direction away from the center is high" holds true over the entire similar gradient direction region Similarly, when the relationship that "the similarity between the gradient direction and the direction away from the center is low" holds true in a given similar gradient direction region as a part of an arc curve detected with the method according to the present embodiment, the similarity between the gradient direction and the direction away from the center is expected to be low in the other similar gradient direction regions.

Thus, the "target pixel" with which the similarity between the gradient direction and the direction away from the center is determined is not necessarily set for each of the similar gradient direction regions. For example, a small number of target pixels (in a narrow sense, a single target pixel) may be set for a single arc curve.

The processing section 100 (in a narrow sense, the bubble region extraction section 140) may extract a region including the representative bubble region as a bubble region.

Thus, the bubble region can be appropriately extracted. In the present embodiment, not the entire bubble region is expected to be detected at the timing where the representative bubble region is detected. For example, in the example illustrated in FIG. 2, the portion C4 is not detected as an arc curve in the first place, or may be detected with the luminance change condition unsatisfied. Thus, the representative bubble region is a region corresponding to C3 (a sector shape with C3 serving as the arch), for example. Thus, in the method according to the present embodiment, in the input image including the entire circular bubble, the representative bubble region might be only a part of the bubble. Thus, when the bubble region is extracted, a region including the representative bubble region is extracted, so that the region failed to be detected at the timing where the representative bubble region is detected can be appropriately determined to be the bubble region. If not the entire bubble region needs to be detected at the timing where the representative bubble region is detected, only a region that is likely to be a bubble (a region with a high likelihood to be a bubble) may be a detection target when the representative bubble region is detected. Thus, a risk of erroneously detecting a region other than the bubble region as the representative bubble region can be reduced. Specifically, based on the representative bubble region illustrated in FIG. 6C, the region illustrated in FIG. 6D including the region can be extracted as the bubble region.

The processing section 100 (in a narrow sense, the bubble region feature value calculation section 130 and the bubble region extraction section 140) may obtain the bubble region feature value based on the feature quantities of the pixels in the representative bubble region, and extract a group of pixels with the feature quantities determined to be similar to the bubble region feature value as a bubble region in the pixels of the input image.

Here, a similarity between the feature value of a given pixel and the bubble region feature value may be obtained based on whether or not the two feature quantities are similar to each other. For example, when the feature value of each pixel and the bubble region feature value are each represented by a five-dimensional vector (x, y, R, G, B), the similarity may be obtained by using Sum of Absolute Difference (SAD), Sum of Squared Difference (SSD), or the like. SAD and SSD are each an index value indicating the level of difference, and thus a larger value of SAD or the like corresponds to a smaller similarity. In the present embodiment, as described above with reference to FIG. 16, the bubble region feature value is supposed to be represented by a distribution (function). For example, when a bubble region feature value is a function f(x, y, R, G, B) of x, y, R, G, B and a feature value of a given pixel is (x', y', R', G', B'), the similarity may be f(x', y', R', G', B') or a value based on this. As described above with reference to FIG. 15 or the like, with the graph cut process, a bubble region is extracted not only based on whether or not the feature value of a given pixel is similar to the bubble region feature value (whether or not the foreground likelihood energy is large), and other factors are taken into consideration (the min cut is searched also based on the energy between adjacent pixels).

Thus, the bubble region can be extracted based on the feature value of the pixel. As described above, in the present embodiment, the region that is likely to be a bubble region can be detected as the representative bubble region. Thus, the bubble region feature value obtained from the representative bubble region is expected to well represent the feature of a bubble. Thus, the level of similarity to the bubble region feature value represents the level of possibility of being a bubble. All things considered, whether or not each pixel corresponds to a bubble region can be accurately determined by using the similarity.

The processing section 100 (in a narrow sense, the bubble region extraction section 140) may segment the input image into regions through the graph cut process based on the bubble region feature value, and extract a region including the representative bubble region as a bubble region.

In this manner, the bubble region can be extracted by the graph cut process. The graph cut process is a widely employed method for segmenting an image into regions, and the min cut (max flow) can be obtained with polynomial time.

The processing section 100 (in a narrow sense, the bubble region extraction section 140) may set a value based on a similarity between a feature value of a pixel in an input image and a bubble region feature value as a cost of a link establishing connection between a node representing the representative bubble region and a node representing the pixel in the input image, and execute the graph cut process based on the cost thus set.

Thus, the cost (energy) based on the similarity between feature quantities can be set to a link between the special node (NA in FIG. 15) representing a bubble and a node representing each pixel. As described above, the bubble region feature value is expected to be a feature value well representing the feature of the bubble. Thus, the similarity between the feature value and the bubble region feature value is suitable as the cost of the link between NA and a node.

The processing section 100 (in a narrow sense, the bubble region extraction section 140) may extract a group of pixels, in pixels in an input image, with a feature value a similarity of which to the bubble region feature value is equal to or larger than a given threshold value, as a bubble region.

Thus, whether or not each pixel corresponds to a bubble region can be determined based on the similarity to the bubble region feature value. This determination using a similarity and a threshold value can be performed to extract a bubble region with a smaller calculation load than in a case where the graph cut process or the like is performed.

The processing section 100 (in a narrow sense, the bubble region feature value calculation section 130) may calculate a feature value based on a pixel value and coordinates, and the bubble region feature value may be a function obtained by approximating a distribution of the feature quantities of pixels in the representative bubble region.

As used herein, "approximating the distribution" is process of obtaining, under an assumption that a group of points each having a value is distributed based on a given distribution function, a parameter of the distribution function based on values of points in the group. For example, assuming that feature quantities are normally distributed, the "function obtained by approximating the distribution" is a function representing the normal distribution. The process of obtaining the function is a process of obtaining an average $\mu$ and dispersion $\sigma^2$ of the normal distribution based on the values of the feature quantities. When a Gaussian mixture model, expressed as linear combination of a plurality of normal distributions, is used as the distribution, a process of estimating (searching for) the average and the dispersion of each normal distribution as well as a parameter for linearly combining the plurality of normal distributions may be performed.

Thus, the pixel values (for example, R, G, B) and the coordinates (x, y) can be used as the feature value. The bubble regions are likely to have similar colors and are likely to be distributed at somewhat similar positions in the input image. Thus, the feature of the bubble can be appropriately expressed with the feature value based on the pixel values and the coordinates. Still, the representative bubble region is expected to include multiple pixels, and values of the feature value based on the pixel values and the coordinates somewhat fluctuate. Thus, in the present embodiment, the bubble region feature value is approximated by a given distribution, so that the bubble region feature value reflecting the fluctuations of values can be obtained. Furthermore, the approximation can be performed by using a Gaussian mixture model or the like, so that the bubble region feature value can be approximated as a combination of a plurality of normal distributions, whereby the bubble region feature value can be appropriately obtained even when there are a plurality of peaks.

The processing section 100 (in a narrow sense, the representative bubble region detection section 120) may detect a region including an arc curve with a central angle that is equal to or larger than a given threshold value, as the representative bubble region.

Thus, even when a non-bubble structure (D3) happens to partially have an arc curve as in the example illustrated in FIG. 14, the arc curve is not used for detecting the representative bubble region, whereby a risk of erroneously detecting the bubble region can be reduced. As used herein, the central angle may be a central angle of a sector shape defined by the arc curve.

The processing section 100 (in a narrow sense, the representative bubble region detection section 120) may detect a region consisting of an arc curve with a radius that is within a given range, as the representative bubble region.

The radius of the arc curve may be regarded as information corresponding to the radius of the circular shape defined by the arc curve. For example, when the arc curve is a part of a true circle, the radius of the arc curve may be the radius of the true circle. When the arc curve is a part of an ellipse, the radius of the arc curve may be the major axis or the minor axis of the ellipse, or a value obtained from these. As described above, an arc curve as a part of an excessively small or large circular shape is excluded from the process of detecting the representative bubble region as described above. Thus, the information used is not limited to the radius, and may include a diameter and an area of a circular shape defined by the arc curve. In other words, the processing section 100 (in a narrow sense, the representative bubble region detection section 120) may detect a region including an arc curve with size information on a circular shape defined by the arc curve that is within a given range as the representative bubble region.

Thus, the arc curve with an excessively small or large radius can be excluded from the process of detecting the representative bubble region. An arc curve of a non-bubble structure may be accidentally detected due to the connection between gradients as described above with reference to FIG. 14. However, the arc curve is expected to be relatively short, because the connection between the gradients is merely an accident. Thus, such an arc curve having a large radius inherently has a small central angle, and thus can be excluded from the process of detecting the representative bubble region with the determination based on the central angle as described above. Unfortunately, the arc curve that is actually short, having a small radius, might have a large central angle (somewhat close to a circle), and thus is difficult to be excluded with the determination based on the central angle. In this context, an arc curve with a large central angle, formed by the accidental connection between gradients, has an extremely small radius. All things considered, the representative bubble region can be accurately detected by excluding the arc curve with an excessively small radius.

On the other hand, when a bubble has a large radius, an object behind the bubble may be observable through the bubble. Thus, even in a situation where bubbles exist, a region corresponding to such bubbles may not preferably be treated as a bubble. A bubble region including no large bubble can be obtained with an arc curve with an excessively large radius excluded from the process.

As used herein, the radius is expected to represent a size (in a unit of pixel, for example) on an image. However, this should not be construed in a limiting sense, and the size in the real space may be used. In the present embodiment, various known methods may be widely employed to obtain the actual size of the object from an input image as the captured image. For example, a distance from the imaging section to the object may be estimated based on the input image, and the actual size may be estimated based on the distance and a status of an optical system (such as the imaging lens system 24).

The image processing device according to the present embodiment may include: the image acquisition section 200 that acquires an input image; and the processing section 100 that implements a process of extracting a bubble region from the input image. The processing section 100 may extract a bubble region from the input image by: detecting arc curves in the input image; detecting a region including at least some of the arc curves as a representative bubble region; obtaining a bubble region feature value based on feature quantities of pixels in the representative bubble region; and segmenting the input image into regions through the graph cut process based on the bubble region feature value.

The image processing device can employ the graph cut process to extract the bubble region from the representative bubble region. Thus, the input image can be segmented into the bubble region and the remaining region with polynomial time. In this process, the bubble region can be accurately extracted with increased stringency of the representative bubble region detection as in the method using the gradient direction described above. The stringency can be increased with a stricter condition for a representative bubble region to be detected as a region that is likely to be a bubble region. At the timing of extracting the representative bubble region, a failure to detect a part of the bubble region will not be fatal, because the process using the graph cut process is performed in the later stage.

JP-A-2012-125469 also discloses a method of extracting a bubble region that is a combination of the arc curve detection and the region segmentation using color information. However, JP-A-2012-125469 determines a region where a large number of arc curves are detected to be a bubble region. Thus, a bubble region is difficult to appropriately extract when the image includes a small number of bubbles. More specifically, in a situation where the number of bubbles is small, the method according to JP-A-2012-125469, which can be successfully performed for determining a portion with an arc curve as a bubble, is difficult to be performed as a process of expanding the bubble region to portions without an arc curve. In this context, in the configuration employing the graph cut process, when a bubble region feature value can be obtained by the processing of detecting the arc curve, the region segmentation can be performed based on relationship (such as similarity) with respect to the bubble region feature value. Thus, the bubble region extraction process can be performed regardless of the number of bubbles in the input image.

The processes of the image processing device or the like according to the present embodiment may be partially or mainly implemented with a program. In such a configuration, the image processing device and the like according to the present embodiment are implemented when a processor such as a CPU executes the program. Specifically, a program stored in a non-transitory information storage device is read out and is executed by the processor such as a CPU. The information storage device (computer-readable device) stores a program and data, and has functions that can be implemented by an optical disk (e.g., CD-ROM and DVD), a hard disk drive (HDD), or a memory (e.g., memory card and ROM). The processor such as a CPU performs various processes according to the present embodiment based on a program (data) stored in the information storage device. Thus, the information storage device stores a program for causing a computer (a device including an operation section, a processing section, a storage section, and an output section) to function as each section according to the present embodiment (program for causing the computer to execute processes of each section).

The present embodiment may be applied to a configuration, such as an endoscope apparatus, where an image is acquired and image processing is executed in the apparatus (in the system), or may be applied to a configuration where image data is accumulated, and a computer system such as a PC perform software processing on the accumulated image data.

The image processing device or the like according to the present embodiment may include a processor and a memory. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application-specific integrated circuit (ASIC). The memory stores a computer-readable instruction. Each section of the image processing device and the like according to the embodiments of the invention is implemented by causing the processor to execute the instruction. The memory may be a semiconductor memory (e.g., SRAM or DRAM), a register, a hard disk, or the like. The instruction may be an instruction included in an instruction set that is included in a program, or may be an instruction that causes a hardware circuit included in the processor to operate.

Although only some embodiments of the present invention and the modifications thereof have been described in detail above, those skilled in the art will readily appreciate that many modifications are possible in the embodiments without materially departing from the novel teachings and advantages of the invention. Accordingly, all such modifications are intended to be included within scope of the invention. For example, any term cited with a different term having a broader meaning or the same meaning at least once in the specification and the drawings can be replaced by the different term in any place in the specification and the drawings. The configurations and the operations of the image processing device and the endoscope apparatus are not limited to those described above in connection with the embodiments. Various modifications and variations may be made of those described above in connection with the embodiments.

What is claimed is:

1. An image processing device comprising a processor including hardware, the processor being configured to:
acquire an input image;
detect an arc curve in the input image;
determine a luminance of pixels in a direction from an inner side toward an outer side of the arc curve;
detect, as a representative bubble region, a region including the arc curve involving a change determined to be an increase in the luminance in the direction from the inner side toward the outer side; and
extract a bubble region from the input image, based on the representative bubble region,
wherein:
the processor determines a similarity between a gradient direction of a pixel value on the arc curve and a direction away from a center of the arc curve,
the processor determines that the change is the increase in the luminance in the direction from the inner side toward the outer side when the similarity is determined to be high, the processor detects the arc curve by combining a plurality of pixels the gradient directions of which have been determined to be similar to each other, and the processor determines whether or not the change is the increase in the luminance in the direction from the inner side toward the outer side of the arc curve, by determining the similarity between the gradient direction at a target pixel in the arc curve and the direction away from the center at the target pixel.

2. The image processing device as defined in claim 1, wherein the processor detects, as the representative bubble region, a region consisting of the arc curve having a central angle that is equal to or larger than a given threshold value.

3. The image processing device as defined in claim 1, wherein the input image comprises an in-vivo image, and wherein the processor performs a process of detecting a region of interest from a region in the in-vivo image excluding the extracted bubble region.

4. An endoscope apparatus comprising the image processing device as defined in claim 1.

* * * * *